United States Patent [19]

Machida et al.

[11] Patent Number: 5,759,866
[45] Date of Patent: Jun. 2, 1998

[54] DEVICE AND METHOD FOR ASSAYING BIOLOGICAL COMPONENTS IN SAMPLE

[75] Inventors: Koichi Machida; Hajime Nakano; Masashi Okamoto; Tohko Okuyama, all of Sanda; Shigeru Fujioka, Tokyo, all of Japan

[73] Assignee: Nihon Medi-Physics Co., Ltd., Hyogo-ken, Japan

[21] Appl. No.: 746,779

[22] Filed: Nov. 15, 1996

[30] Foreign Application Priority Data

Nov. 15, 1995 [JP] Japan ................... 7-321014

[51] Int. Cl.[6] .................. G01N 33/53; G01N 33/543
[52] U.S. Cl. .................. 436/518; 436/514; 436/501; 436/523; 435/7.1; 435/7.93; 435/7.94; 435/7.5
[58] Field of Search .................. 435/7.1, 7.93, 435/7.94, 7.5; 436/501, 518, 523, 514

[56] References Cited

U.S. PATENT DOCUMENTS 5,601,991  2/1997  Oberhardt ................... 435/7.91

FOREIGN PATENT DOCUMENTS

| | | |
|---|---|---|
| 0098590 | 1/1984 | European Pat. Off. . |
| 0303110 | 2/1989 | European Pat. Off. . |
| 0679893 | 11/1995 | European Pat. Off. . |
| 63-177059 | 7/1988 | Japan . |
| 723891 | 3/1995 | Japan . |
| 0 698 413 A2 | 2/1996 | Japan . |
| WO9112528 | 8/1991 | WIPO . |
| WO9635123 | 11/1996 | WIPO . |

*Primary Examiner*—Toni R. Scheiner
*Attorney, Agent, or Firm*—Sughrue, Mion, Zinn, Macpeak & Seas, PLLC

[57] ABSTRACT

By using an assay device comprising a sample-receiving port, a pump-connection port, a sample-treating zone which is provided with a labeled substance with a label, a sample-treating and optical-measuring zone which has a porous material having immobilized thereto one of a specifically binding pair, and a pathway interconnecting these zones and ports, wherein the sample-treating zone and the sample-treating and optical-measuring zone are positioned between the sample-receiving port and the pump-connection port;

or by using an assay device comprising a sample-receiving port, a pump-connection port, a sample-treating and optical-measuring zone which has a porous material having immobilized thereto a labeled substance with a label and one of a specifically binding pair, and a pathway interconnecting these zone and ports, wherein the sample-treating and optical-measuring zone is positioned between the sample-receiving port and the pump-connection port, biological components can be quantitatively determined by immunoassay in a simple manner.

16 Claims, 1 Drawing Sheet

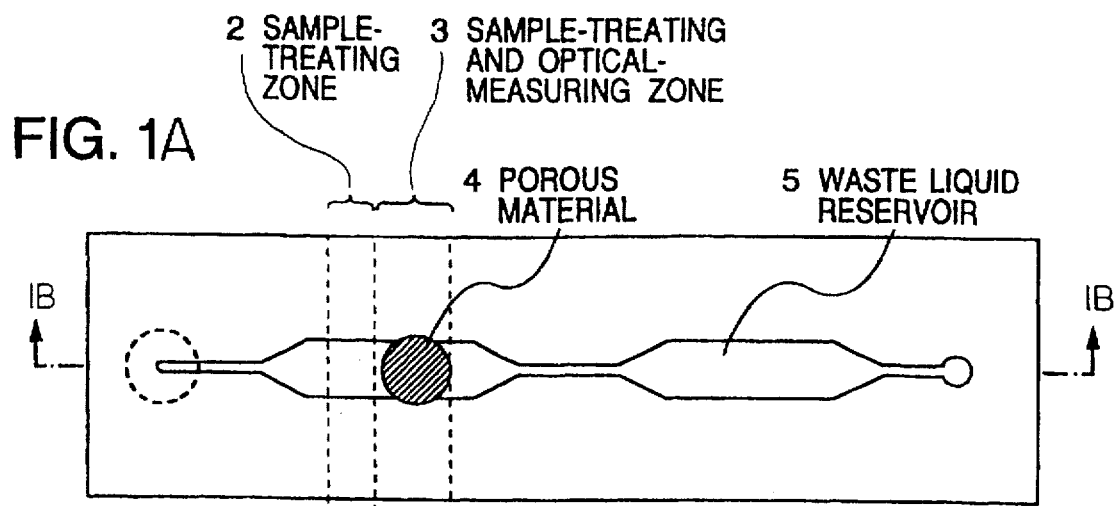
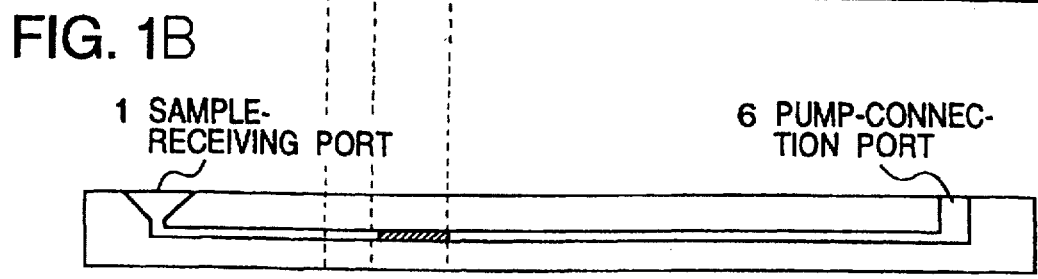
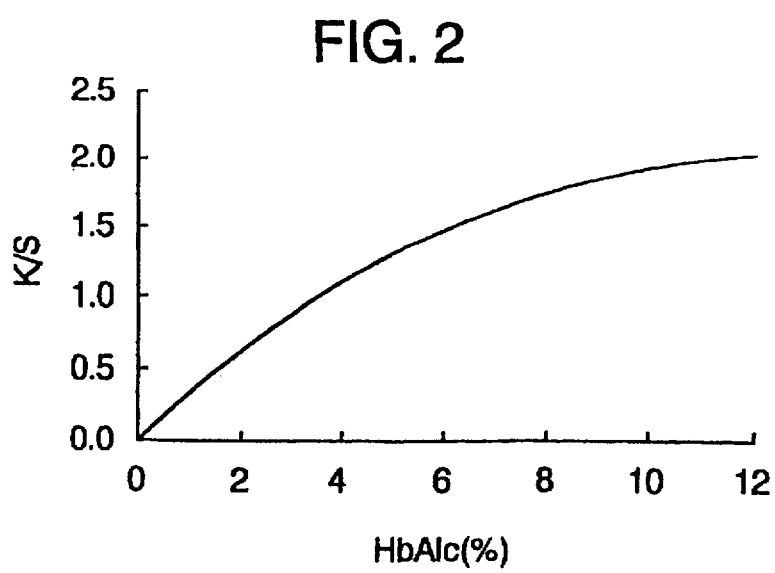

DEVICE AND METHOD FOR ASSAYING BIOLOGICAL COMPONENTS IN SAMPLE

BACKGROUND OF THE INVENTION

1. Field of the Invention

The present invention relates to a device for assaying a component in a biological fluid such as human or animal blood or urine in a simple manner, utilizing an immune reaction. The present invention also relates to an assay method using such a device.

2. Related Art Statement

For the determination of biological components which utilizes an immune reaction, immunoassay using a radioisotope as a label was its beginning; since then fluorescent substances or enzymes have been developed as the label. These assay methods have been developed in parallel with the development for conducting a part or all of manual operations in complicated immunoassay on automated devices to release an operator from arduous operations. A main cause for the complicated operations in immunoassay utilizing an immune reaction is observed in B/F separation.

B/F separation is an operation for physically separating antigen-antibody complexes (bound species) and unbound antibodies or antigens (free species) from each other. A conventional method for B/F separation involves the steps of immobilizing either one of the specific binding pair such as an antigen-antibody complex onto microplates, porous beads, glass fibers, nitrocellulose filters, etc.; reacting the other of the specific binding pair with the immobilized species; and washing out the unbound species. The operations required for this conventional method have been conducted on commercially available devices such as STRATUS (trademark) manufactured by American Hospital Supply Corporation, ID-1000 manufactured by Toyobo Co., Ltd., and the like. However, a large-scaled and complicated device is required, because reaction solutions or washing liquid should be vertically flown down onto membranes or filters.

On the other hand, manual immunoassay devices utilizing immunochromatography have also been developed to simplify the operations. A representative manual device is a narrow strip of nitrocellulose filter for the examination of fecal occult blood. In the device, an excess of colloidal gold-labeled antibody is impregnated with a glass fiber filter, dried and immobilized onto at one end of the nitrocellulose filter, an anti-IgG antibody is immobilized at the other end, and an anti-human hemoglobin antibody is immobilized in a band form around the center. Hemoglobin present in a sample solution is assayed with the device by the following procedures. A dilution of a feces sample is dropped onto a glass fiber filter. A hemoglobin in the sample solution together with an excess amount of the labeled antibody in the glass filter flows toward the anti-IgG antibody, while reacting with each other. The hemoglobin reacts with anti-human hemoglobin antibody at the central band, where as a result the labeled antibody is immobilized. An excess amount of the labeled antibody and substances which have not reacted with the anti-human hemoglobin antibody are washed out toward the anti-IgG antibody-immobilized end of the filter, and the excess labeled antibody binds to the filter end to which the anti-IgG antibody is immobilized. By the presence of colloidal gold at this end, it is confirmed that the sample solution have been supplied in a sufficient volume. The presence or absence of colloidal gold is visually checked at the anti-human hemoglobin antibody-immobilized band thereby to detect the presence of hemoglobin to be analyzed in the sample solution. As described above, the reagents for immunoassay enables to assay the presence of hemoglobin in the sample solution in a simple manner. In the reagents, however, a spreading velocity of reaction solutions on the filter depends upon chromatographic action (i.e., capillary action) of a porous medium so that the spreading velocity (reaction time in this case) can be hardly controlled. Furthermore, time periods for antigen-antibody reaction and for B/F separation cannot be controlled due to the physical properties of a sample, the pore diameter of a porous support or its uneven density which causes uneven spreading velocity. For these reasons, only qualitative results can be obtained with the above reagents.

Japanese Patent KOKAI (Laid-Open) No. 7-159398 discloses a device for immunoassay which is employed to quantitatively determine biological components in body fluid on immunochromatography. The device contains a labeled substance-immobilized zone in which five chambers are provided. The device allegedly enables to determine quantitatively an analyte in body fluids, because the number of the chambers form different color changes correspondingly to the concentration of the analyte in a liquid sample. However, even if the color of the chambers is distinguishable in five stages, such an assay is insufficient for quantitative assay but will merely deserve semi-quantitative assay.

SUMMARY OF THE INVENTION

In view of the foregoing problems encountered in the prior art, it is an object of the present invention to eliminate these problems and provide a device appropriately applicable to quantitative immunoassay in a simple manner.

The present inventors extensively researched to develop a satisfactorily assay device for use in quantitative immunoassay. As a result, it has been found that by providing a device comprising a sample-treating zone, a sample-treating and optical-measuring zone having a porous material and a pathway inter-connecting these zones arranged so as to be capable of controlling the supply of a liquid sample through a pump, simple immunoassay can be made quantitatively. The present invention has thus been achieved.

That is, a first aspect of the present invention relates to a device for assaying a biological component in a sample comprising:

a sample-receiving port, a pump-connection port, a sample-treating zone which is provided with a labeled substance with a label, a sample-treating and optical-measuring zone which has a porous material having immobilized thereto one of a specifically binding pair, and;

a pathway interconnecting these zones and ports, wherein the sample-treating zone and the sample-treating and optical-measuring zone are positioned between the sample-receiving port and the pump-connection port.

A second aspect of the present invention relates to a device for assaying a biological component in a sample comprising:

a sample-receiving port, a pump-connection port, a sample-treating and optical-measuring zone which has a porous material having immobilized thereto a labeled substance with a label and one of a specifically binding pair, and a pathway interconnecting these zone and ports, wherein the sample-treating and optical-measuring zone is positioned between the sample-receiving port and the pump-connection port.

A third aspect of the present invention relates to a device in the first or second aspect, wherein:

the labeled substance is a labeled substance which specifically binds to the biological component at one recognition site thereof, and one of the specifically binding pair immobilized on the porous material is a substance which specifically reacts with the biological component at the other recognition site thereof.

A fourth aspect of the present invention relates to a device in the first aspect, wherein:

the sample-treating zone is provided with a labeled substance which is the same substance as the biological component or a modified substance thereof, and a substance which specifically reacts with the biological component is immobilized on the porous material.

A fifth aspect of the present invention relates to a device in the first or second aspect, wherein:

the sample-treating zone is provided with a labeled substance which specifically binds to the biological component at one recognition site thereof, and a substance which specifically reacts with the biological component at the other recognition site thereof, and a substance capable of binding to the substance which specifically reacts with the biological component at the other recognition site thereof is immobilized on the porous material.

A sixth aspect of the present invention relates to a device in the fifth aspect, wherein:

the sample-treating zone is provided with a labeled first antibody which specifically binds to the biological component at one recognition site thereof, and a complex of biotin and a second antibody which specifically reacts with the biological component at the other recognition site thereof, and avidin or streptoavidin is immobilized on the porous material.

A seventh aspect of the present invention relates to a method for assaying a biological component in a sample which comprises the steps of:

supplying the sample through a sample-receiving port in the device according to any one of the first to sixth aspects;

controlling supply of the sample with a pump; and measuring the label which is captured in the porous material to determine the biological component in a sample.

BRIEF DESCRIPTION OF DRAWING

FIG. 1 shows a representative example of the assay device according to the present invention, in which the upper part is a cross-sectional view of the device shown in the lower part which is cross-sectionally cut at B–B'. The lower part is a cross-sectional view of the device shown in the upper part which is cross-sectionally cut at A–A'.

FIG. 2 indicates a calibration curve obtained in the example of the present invention.

DETAILED DESCRIPTION OF THE INVENTION

In the assay device of the present invention, the sample-treating zone may be provided between the sample-receiving port and the sample-treating and optical-measuring zone. Alternatively, the sample-treating zone may be provided between the sample-treating and optical-measuring zone and the pump-connection port.

The assay device of the present invention may further comprise a waste liquid reservoir for storing washing liquid flowed out from the sample-treating and optical-measuring zone.

As samples which are applicable to the assay device of the present invention for determining components in biological fluid, there may be typically exemplified human and animal blood, urine and feces. It is preferred that blood and feces be diluted and the dilution is used as a sample, because the dilution may also function as a washing liquid for B/F separation described hereinafter. The assay device of the present invention is advantageously employed for the determination of hemoglobin $A_{1c}$ (hereinafter sometime referred to as "$HbA_{1c}$") and a diabetic marker represented by glucosylated albumin, and also applicable to diagnosis of pregnancy, fecal occult blood, viral infection, etc.

The term "specifically binding pair" is used herein to mean a combination of one pair of substances capable of specifically binding to each other, as exemplified in an antigen-antibody reaction, avidin- or streptoavidin-biotin binding or a boronate-cis-diol binding.

Examples of the label which may be advantageously used in the present invention include colloid of metals such as gold, silver and selenium; dyes such as a colored latex; and enzymes such as an alkaline phosphatase and a peroxidase.

Where an enzyme is employed as the label, an excess amount of a sample is supplied to wash the device and then a solution containing reagents capable of reacting with the enzyme to produce a color signal is applied to the porous material through the pathway of the assay device. Alternatively, these reagents may be previously contained in the sample.

Representative examples of the porous material which may be preferably employed in the present invention are nitrocellulose filter, cellulose acetate filter, nylon membrane, filter paper and glass fiber filter.

Hereinafter the present invention will be described in more detail, by referring to the drawings.

FIG. 1 shows a representative example of the assay device according to the present invention, in which the upper drawing is a cross-sectional view of the device shown in the lower drawing which is cross-sectionally cut at B–B'. The lower drawing is a cross-sectional view of the device shown in the upper drawing, which is cross-sectionally cut at A–A'.

Any material may be employed to form the assay device so long as it is a light-transmitting, liquid-impermeable and readily processable material. For this purpose, a plastic material is suitable. Representative examples of the plastic material include polystyrol resin, acryl resin, polyvinyl chloride resin, polycarbonate resin, polyethylene resin, polypropylene resin, polyethylene resin and terephthalate resin.

Two plate elements composed of these materials are combined or stuck together to form a pathway in a thin layer form as a whole, as shown in FIG. 1.

The sample applied to the sample-receiving port (1) is moved to the pump-connection port (6) from the sample-receiving port by means of the pump (not shown) connected with the pump-connection port.

In the assay device of the present invention, the sample liquid itself may be also used as washing liquid for B/F separation. Therefore, it is not particularly necessary to provide washing liquid. Further, the assay device may comprise a waste liquid reservoir for storing the washing liquid, whereby the device is prevented from dirt, and the device used may be scrapped as it is.

According to the present invention, the sample is moved within the pathway under control by means of the pump, so that the assay device is not adversely affected by physical properties such as of the liquid sample, unlike a conventional immunochromatography assay in which a sample and reaction solutions are moved in porous materials The assay device of the present invention may be applied to both sandwich and competitive methods for immunoassay, depending upon the kind of reagents provided in the pathway or the combination of reagents binding to the porous material.

Where the assay device of the present invention is used for immunoassay using a sandwich method, a substance (e.g., a first antibody to a biological component to be assayed) capable of binding to a biological component is labeled with a label to form a labeled substance (hereinafter referred to as "first substance"), which is deposited on the sample-treating zone in an excess amount. The first substance may be deposited on the sample-treating zone with a conventional manner, e.g., coating or printing.

When the sample is transferred to the sample-treating zone (2), the biological component in the sample reacts with the first substance on the sample-treating zone to form a complex. Since the first substance on the sample-treating zone is provided at an amount excess to the biological component to be assayed in the sample, both the first substance to which the biological component has been bound and the unbound first substance exist after the binding reaction.

After a time period required for the reaction in the sample-treating zone has passed, the sample is then sucked by means of the pump to transfer to the sample-treating and optical-measuring zone.

In the sample-treating and optical-measuring zone (3), positioned is a substance (hereinafter referred to as "second substance") which is capable of binding to the complex of the first substance and the biological component but which is not capable of binding to the first substance to which the biological component has not bound. The second substance is immobilized on the porous material (4) in the zone (3). The immobilization of the second substance on the porous material may be achieved by a conventional physicochemical means.

The second substance is a substance capable of recognizing a recognition site in the biological component, which is different from the recognition site recognized by the first substance. The second substance is exemplified by a second antibody to the biological component. After a time required for the reaction in the sample-treating and optical-measuring zone has passed, the sample is transferred to a waste liquid reservoir (5). At this moment, the first substance bound to the biological component is captured and remained in the porous material at the zone (3), since the second substance immobilized on the porous material reacts with and binds to the biological component. On the other hand, the first substance unbound to the biological component is not captured and then is transferred to the waste liquid reservoir (5). By optically measuring the amount of the label in the first substance captured in the porous material, the biological component to be assayed can be determined.

In this embodiment of the sandwich assay as described above, the first and second substances may be positioned in the same zone, since these substances do not react with each other. That is, this embodiment corresponds to the assay device in the second aspect of the present invention as described hereinbefore, in which the labeled substance (first substance) and the porous material are both provided in the sample-treating and optical-measuring zone.

In the sandwich method as described above, avidin or streptoavidin may be alternatively immobilized on the porous material. In this embodiment, there are provided in the sample-treating zone both the first substance (e.g., a first antibody and a labeled substance with a label) in an amount excess to the biological component in the sample and the second substance (e.g., a second antibody) capable of binding to the biological component in the sample at the recognition site different from the recognition site of the first substance, to which second substance biotin is further bound. In this embodiment, the biological component in the sample is sandwiched between the first and second substances to form a complex in the sample-treating zone. The biotin bound to the second substance in the complex is bound to avidin or streptoavidin immobilized on the porous material in the sample-treating and optical-measuring zone so that the complex is captured in the porous material. An excess of the first substance is washed out by the sample flowing thereafter. Accordingly, the biological component can be assayed by optically measuring the amount of the label in the complex captured in the porous material.

It is commercially advantageous to utilize the avidin- or streptoavidin-biotin binding as described above, since the avidin or streptoavidin immobilized on the porous material may be commonly used independently from a biological component to be assayed.

Where the assay device of the present invention is applied to competitive immunoassay, the sample-treating zone is provided with a labeled substance prepared by labeling with a label the same substance as the biological component to be assayed or a modified substance thereof. The modified substance referred to herein is used to mean a substance which is by somewhat modifying the same substance as the biological component in such a way that a label may be easily bound to the substance.

In the porous material, there is previously immobilized a substance (e.g., an antibody to the biological component to be assayed) capable of specifically binding to the biological component to be assayed in the sample. When the sample is supplied through the sample-receiving port, the sample is mixed with the same substance as the biological component or its modified substance which is labeled with a label and which is provided in the sample-treating zone. The mixture is then transferred to the porous material. The substance capable of specifically binding to the biological component to be assayed, which substance is immobilized on the porous material, competitively binds to the biological component in the sample and to the same substance as the biological component or its modified substance which is labeled with a label and which is provided in the sample-treating zone, in proportion to their concentrations, respectively. Therefore, by measuring the concentration of the label which is still remained after the reaction and washing, the concentration of the biological component to be assayed in the sample can be determined based on the amount of the same substance as the biological component to be assayed or its modified substance, which substance is labeled with a label and which is provided in the sample-treating zone.

In the assay device of the present invention, the sample-treating zone may be positioned preferably between the sample-receiving port and the sample-treating and optical-measuring zone, or may also be positioned at the pump-connection port side in the sample-treating and optical-measuring zone. In this case, the optical background value of the sample is previously measured after impregnated into the porous material. Then, the sample is reacted with the first and second substances, and returned to the sample-treating zone by means of the pump.

According to the present invention, the label in the porous material is optically measured and hence, the zone with the porous material functions as the sample-treating and optical-measuring zone. The optical measurement may be conducted by either transmitted light or reflected light.

EXAMPLE

Hereinafter the present invention is more specifically described with reference to Example for assaying hemoglobin $A_{1c}$. In the Example, a complex of a blue micro particle and an anti-human $HbA_{1c}$ mouse monoclonal antibody is used as the first substance, and an anti-human hemoglobin antibody is used as the second substance.

a) Preparation of the first substance and the second substance a-1) Preparation of an anti-hemoglobin antibody-immobilized filter (immobilization of the second substance to the porous material)

An anti-hemoglobin antibody was mixed with neutral phosphate buffer at a concentration of 300 µg/ml. The mixture was impregnated with a nitrocellulose filter (Millipore) (hereinafter abbreviated as "NCF") having a pore size of 8 µm. While mildly shaking at room temperature for 2 hours, the anti-hemoglobin antibody was immobilized on NCF. The amount of the antibody immobilized was 45 µg/cm².

In order to prevent undesired non-specific adsorption, NCF was rinsed with neutral phosphate buffer and then immersed in neutral phosphate buffer containing 1% milk casein. After mildly shaking for 2 hours at room temperature for blocking, NCF was washed with neutral phosphate buffer.

NCF was dried at 37° C. for an hour and punched in a size of 5 mmφ to obtain an anti-hemoglobin antibody-immobilized filter.

a-2) Preparation of anti-hemoglobin $A_{1c}$ monoclonal antibody-immobilized blue micro particles (hereinafter abbreviated as "bmP") (preparation of the first substance With HEPES buffer anti-hemoglobin $A_{1c}$ monoclonal antibody and blue micro particles were mixed in amounts of 1.5 mg/ml and 1.25%, respectively. Blue colored polystyrene beads (Bangs Laboratories Inc.) having a diameter of 200 nm were employed as the blue micro particles.

The mixture was mildly shaken for 2 hours at room temperature to immobilize an anti-hemoglobin A1c monoclonal antibody to the blue micro particles. The amount of the immobilized antibody was 1 mg per ml of 1% blue micro particles. The resulting solution was centrifuged for an hour at 30,000×G. The supernatant was removed to isolate the blue micro particles.

The thus obtained blue micro particles were suspended in PIPES buffer supplemented with 1% milk casein in the same volume of the removed supernatant, which was mildly shaken for 2 hours at room temperature for blocking. After the blocking, centrifugation was performed for an hour at 30,000×G to remove the supernatant. The precipitate was washed by resuspending the same in HEPES buffer. The washing operation was repeated 3 times for thorough washing. The precipitate was again resuspended in HEPES in a concentration of 2% to obtain bmP.

a-3) Preparation of the device assay bmP was deposited on the sample-treating zone formed between two polystyrene plates, and then dried. Next, the anti-hemoglobin antibody-immobilized filter was inserted into the sample-treating and optical-measuring zone and combined with the sample-treating zone to prepare the assay device as shown in FIG. 1.

The thickness of the pathway between the sample-receiving port and pump-connection port was 0.5 mm at the waste liquid reservoir and was 0.2 mm at the other parts.

b) Assay b-1) Preparation of $HbA_{1c}$ sample (preparation of sample)

Red blood cells were isolated by centrifugation from human blood which contained $HbA_{1c}$ at various concentrations (%). The isolated red blood cells were suspended in physiological saline and washed. After centrifugation, the supernatant was removed and the precipitates were resuspended in physiological saline. This procedure was repeated 3 times to thoroughly wash the red blood cells. Finally, the red blood cells were suspended in HEPES buffered physiological saline (containing hemoglobin denaturant) at an appropriate concentration. Each suspension was repeatedly freezed and fused to cause haemolysis for use as a sample.

As a blank sample of 0% $HbA_{1c}$, a purified $HbA_0$ (EXOCELL) was employed.

b-2) Reaction

After 100 µl of the sample was dropped onto the sample-receiving port, the device was sucked by a suction pump until the edge of the liquid sample reached the tip of the dried bmP, whereby bmP was dispersed. The liquid sample was allowed to stay at this position for 3 minutes, where bmP was reacted with $HbA_{1c}$ in the sample. Suction was again performed to force the edge of the liquid sample to reach the tip of the anti-hemoglobin antibody-immobilized filter. The sample was allowed to stay at this position for 5 minutes to bind a $HbA_{1c}$-bmP complex and hemoglobin to the anti-hemoglobin antibody, where only a definite amount of hemoglobin was bound to the anti-hemoglobin antibody so that bmP in response to the concentration (%) of $HbA_{1c}$ in hemoglobin was bound to the filter.

Thereafter the volume of 70 µl was sucked, and the free bmP and $HbA_{1c}$-bmP complex were washed out with an excess of the sample, which was then flowed into the waste liquid reservoir.

b-3) Optical measurement

A reflectance (R%) of the anti-hemoglobin antibody-immobilized filter was measured at 640 nm, using a color difference meter (Nippon Denshoku Co., Ltd.).

b-4) Calibration curve

The reflectance obtained was converted into K/S value according to the equation given below. The K/S value was plotted for the concentration (%) of $HbA_{1c}$ separately determined by HPLC to obtain the calibration curve as shown in FIG. 2.

$$K/S = \frac{(1 - R\%)^2}{2 R\%}$$

As described above in detail, according to the present invention, the immunoassay can be quantitatively performed in a simple manner.

What is claimed is:

1. A device for assaying a biological component in a sample comprising:

a sample-receiving port, a pump-connection port, a sample-treating zone which is provided with a labeled substance with a label, a sample-treating and optical-measuring zone which has a porous material having immobilized thereto one of a specifically binding pair, and a pathway interconnecting these zones and ports;

wherein the sample-treating zone and the sample-treating and optical-measuring zone are positioned between the sample-receiving port and the pump-connection port.

2. A device for assaying a biological component in a sample comprising:

a sample-receiving port, a pump-connection port, a sample-treating and optical-measuring zone which has a porous material having immobilized thereto a labeled substance with a label and one of a specifically binding pair, and a pathway interconnecting these zone and ports;

wherein the sample-treating and optical-measuring zone is positioned between the sample-receiving port and the pump-connection port.

3. A device according to claim 1, wherein:

the labeled substance is a labeled substance which specifically binds to the biological component at one recognition site thereof, and one of the specifically binding pair immobilized on the porous material is a substance which specifically reacts with the biological component at the other recognition site thereof.

4. A device according to claim 2, wherein:

the labeled substance is a labeled substance which specifically binds to the biological component at one recognition site thereof, and one of the specifically binding pair immobilized on the porous material is a substance which specifically reacts with the biological component at the other recognition site thereof.

5. A device according to claim 1, wherein:

the sample-treating zone is provided with a labeled substance which is the same substance as the biological component or a modified substance thereof, and a substance which specifically reacts with the biological component is immobilized on the porous material.

6. A device according to claim 1, wherein:

the sample-treating zone is provided with a labeled substance which specifically binds to the biological component at one recognition site thereof, and a substance which specifically reacts with the biological component at the other recognition site thereof, and a substance capable of binding to the substance which specifically reacts with the biological component at the other recognition site thereof is immobilized on the porous material.

7. A device according to claim 2, wherein:

the sample-treating zone is provided with a labeled substance which specifically binds to the biological component at one recognition site thereof, and a substance which specifically reacts with the biological component at the other recognition site thereof, and a substance capable of binding to the substance which specifically reacts with the biological component at the other recognition site thereof is immobilized on the porous material.

8. A device according to claim 6, wherein:

the sample-treating zone is provided with a labeled first antibody which specifically binds to the biological component at one recognition site thereof, and a complex of a biotin and a second antibody which specifically reacts with the biological component at the other recognition site thereof, and avidin or streptoavidin is immobilized on the porous material.

9. A device according to claim 7, wherein:

the sample-treating zone is provided with a labeled first antibody which specifically binds to the biological component at one recognition site thereof, and a complex of biotin and a second antibody which specifically reacts with the biological component at the other recognition site thereof, and avidin or streptoavidin is immobilized on the porous material.

10. A device according to any one of claims 1, 3, 5, 6, 7, 8 or 9, wherein the sample-receiving zone is positioned between the sample-receiving port and the sample-treating and optical-measuring zone.

11. A device according to any one of claims 1 through 9, wherein the label is a metal colloid or colored latex particle.

12. A device for assay according to any one of claims 1 through 9, wherein the label is an enzyme.

13. A device according to any one of claims 1 through 9, wherein each of the sample-treating zone, sample-treating and optical-measuring zone and pathway is formed by a thin layer.

14. A device according to anyone of claims 1 through 9, which further comprises a waste liquid reservoir for storing washing liquid flowed out from the sample-treating and optical-measuring zone.

15. A device according to claim 14, wherein the waste liquid reservoir is formed by a thin layer.

16. A method for assaying a biological component in a sample which comprises the steps of:

supplying the sample through a sample-receiving port in the device according to any one of claims 1 through 9;

controlling supply of the sample with a pump; and, measuring the label which is captured in the porous material to determine the biological component in a sample.

* * * * *